US00PP12621P2

(12) United States Plant Patent

Yanny

(10) Patent No.: US PP12,621 P2

(45) Date of Patent: May 14, 2002

(54) *MALUS SARGENTII* PLANT NAMED 'SELECT A'

(75) Inventor: Michael D. Yanny, Milwaukee, WI (US)

(73) Assignee: Johnson's Nursery, Inc., Menomonee Falls, WI (US)

( * ) Notice: Subject to any disclaimer, the term of this patent is extended or adjusted under 35 U.S.C. 154(b) by 0 days.

(21) Appl. No.: 09/274,573

(22) Filed: Mar. 23, 1999

(51) Int. Cl.[7] ..... A01H 5/00

(52) U.S. Cl. ..... Plt./173

(58) Field of Search ..... Plt./173

*Primary Examiner*—Bruce R. Campell
*Assistant Examiner*—Anne Marie Grünberg
(74) *Attorney, Agent, or Firm*—W. Dennis Drehkoff; Ladas & Parry

(57) ABSTRACT

A distinctive variety of *Malus sargentii*, most often referred to as a flowering crabapple tree, possesses a compact, upright growth habit, a colorful persistent fruit that remains ornamental long into the winter and is resistant to Apple Scab disease.

11 Drawing Sheets

The present invention relates to a new and distinctive variety of *Malus sargentii*, commonly referred to as a flowering crabapple tree, originating from my discovery of a seedling from Johnson's Nursery, Jackson, Wis. with *Malus sargentii* being the unnamed seed parent typical of the species. It is not patented. The pollen patent is unknown.

The colorful tree of my new variety possesses many exceptional characteristics includings:

(a) A compact, upright growth habit when young having a rounded symmetrical shape, which spreads upon maturity, (b) A colorful persistent fruit that remains ornamental much later into the winter season than its parent, and (c) Proven resistance to Apple Scab disease.

The new variety can be grown to serve as an ornamental and to provide colorful fruit for extended periods of time, into the winter season.

The tree has been reproduced outdoors in Menomonee Falls, Wis. where asexual reproduction has taken place by grafting onto an understock of EMLA 111. The rootstock is unpatented. The plant has also been produced from rooted cuttings in Menomonee Falls, Wis. and is considered own-root. The asexual reproduction shows that the aforementioned and all other distinctive characteristics are transmitted from one generation to another, and that the plant reproduces true to type.

The new variety has been named the *Malus sargentii* 'Select A' variety.

BRIEF DESCRIPTION OF THE ILLUSTRATIONS

The accompanying illustrations show typical specimens of the vegetative growth, flowers and fruit of the new variety in different stages of development, mainly mature growth, and as depicted in color as nearly true as it is reasonably possible to make the same in a color illustration of this character.

The fruit was picked, on the same day, from the parent *Malus sargentii* tree and the original *Malus sargentii* 'Select A' tree and photographed. The fruit was not wind fall material. Much of the fruit on the *Malus sargentii* tree from which I had picked had been eaten by birds. The birds eat the softened fruit and leave the hard ones. The fruit of *Malus sargentii* softens quickly after hard freezes in mid to late fall. As the fruit softens it begins to lose moisture and shrivels, losing its ornamental appeal. *Malus sargentii* 'Select A' has a great majority of its fruit that remains hard into the winter. They are less affected by hard frosts. Its large quantities of hard fruit remain colorful into the winter and fewer are taken by birds. The *Malus sarentii* 'Select A' fruit do not shrivel to the extent of *Malus sargentii* in fall.

Figure 1:
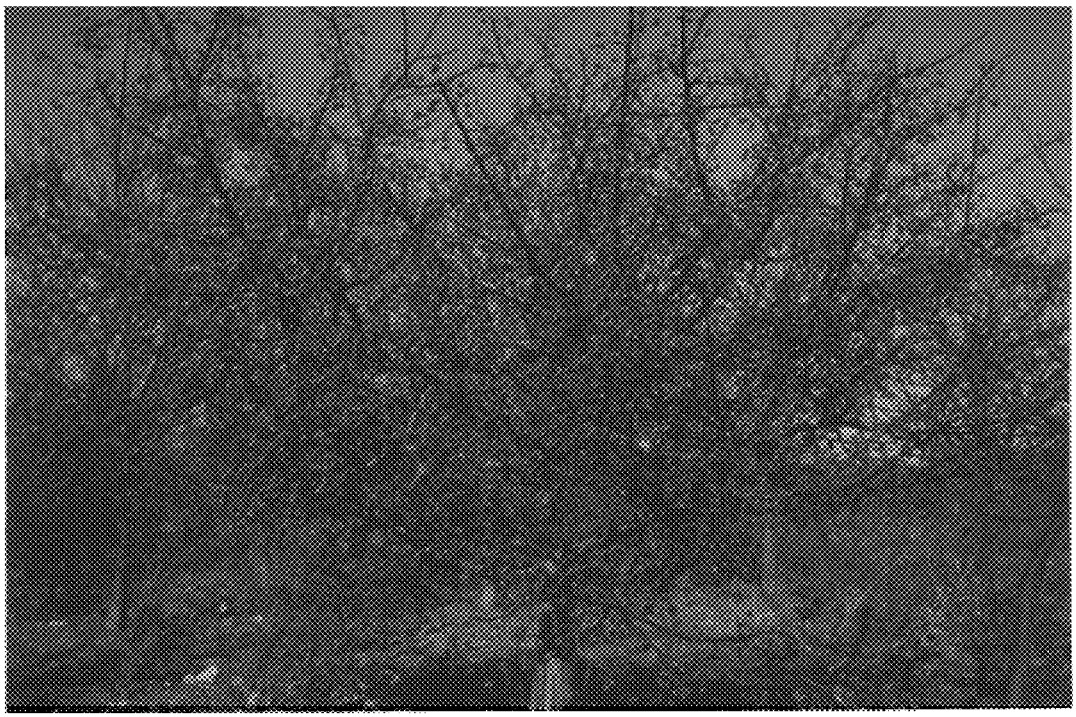
FIG. 1 illustrates a mature tree with a compact growth habit with a spreading symmetrical shape of the crabapple tree.
Figure 2:
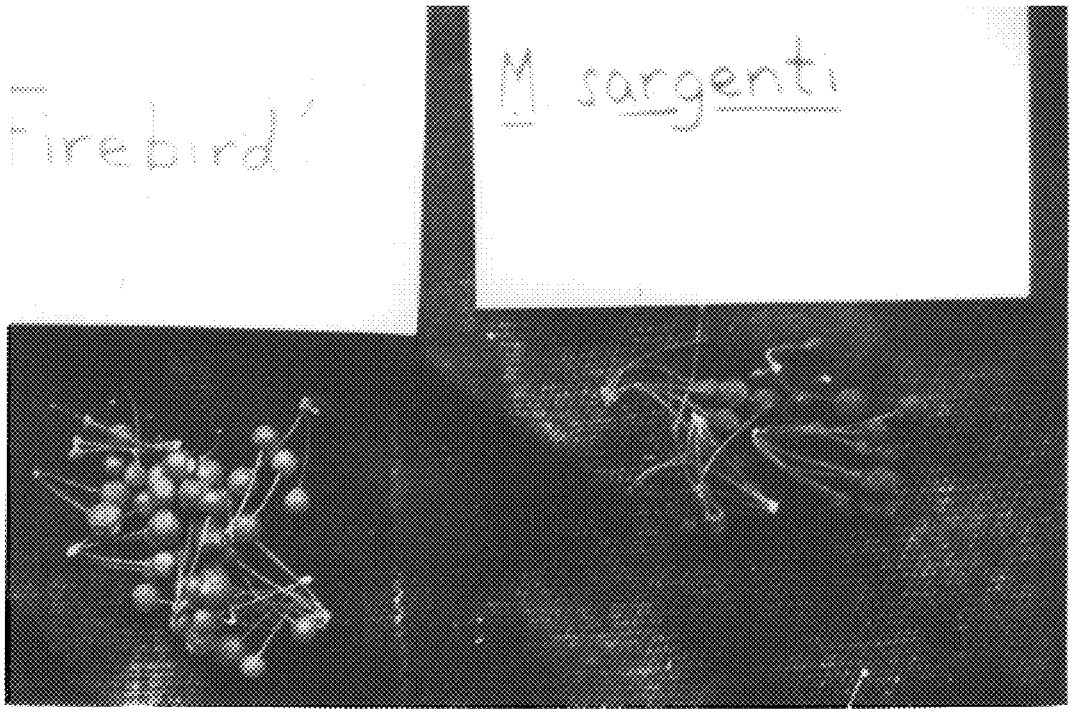
FIG. 2 illustrates the colorful, plump fruit of the crabapple hybrid labeled 'FIREBIRD' (*M. sargentii* 'Select A') and its parent *M. sargentii*. The photograph was taken in late December in southeastern Wisconsin.
Figure 3:
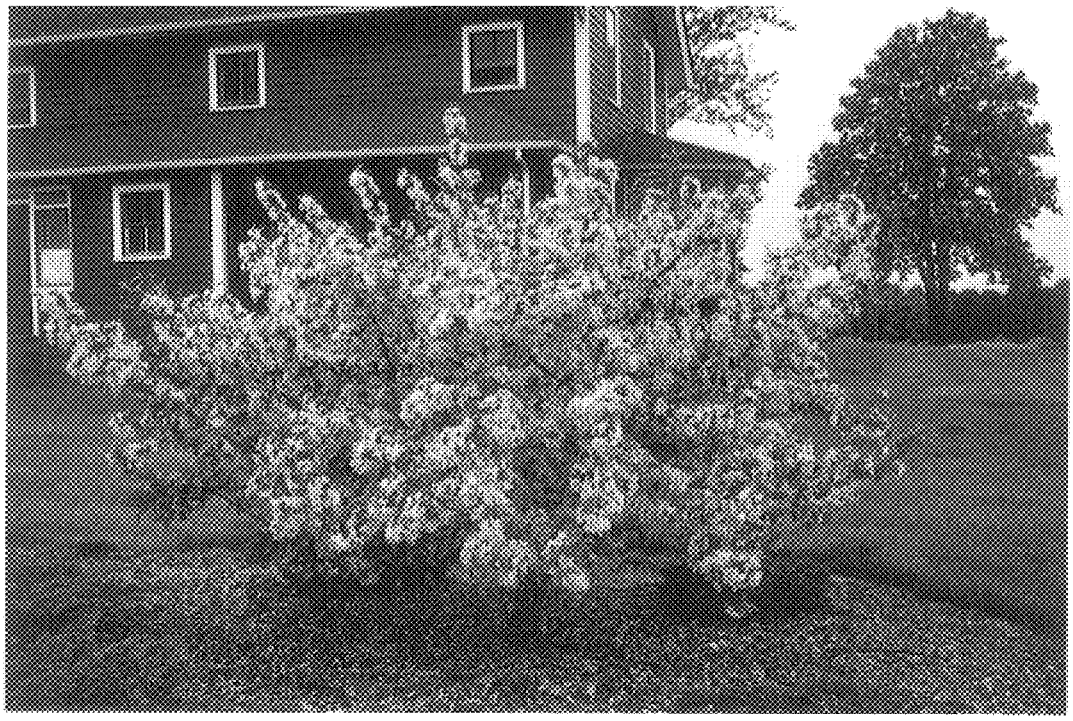
Figure 4:
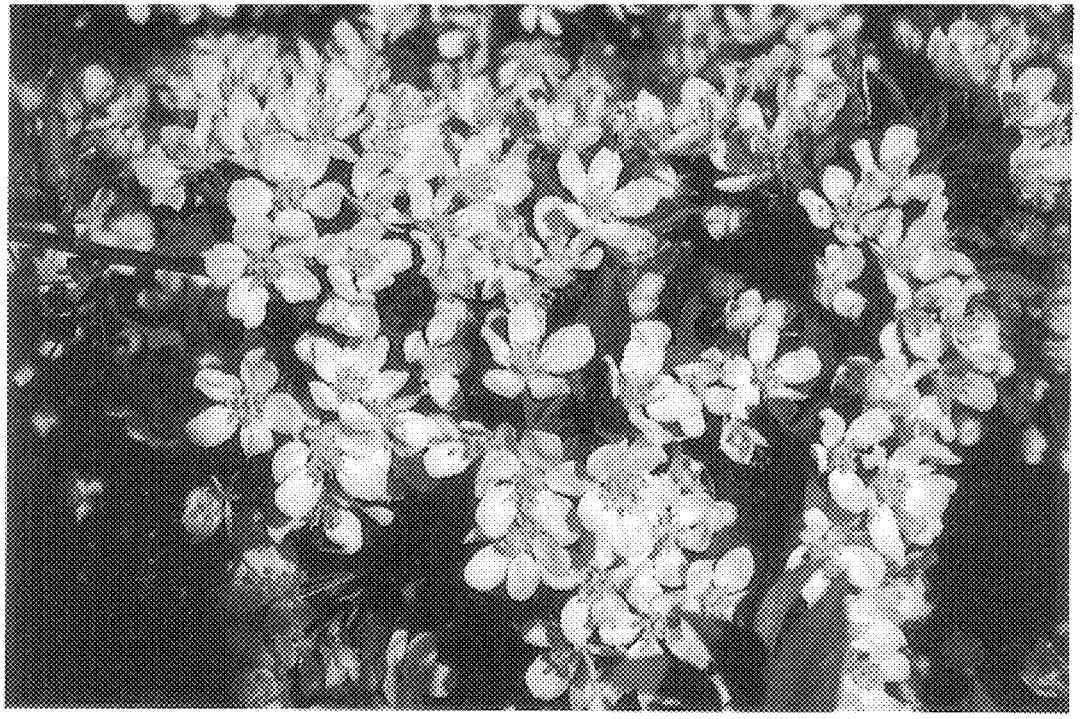

FIGS. 3 and 4 show a true representation of the flowers on *Malus sargentii* 'Select A'. The pictures were taken May 17, 1999 of the 'original Select A' plant.

Figure 5:
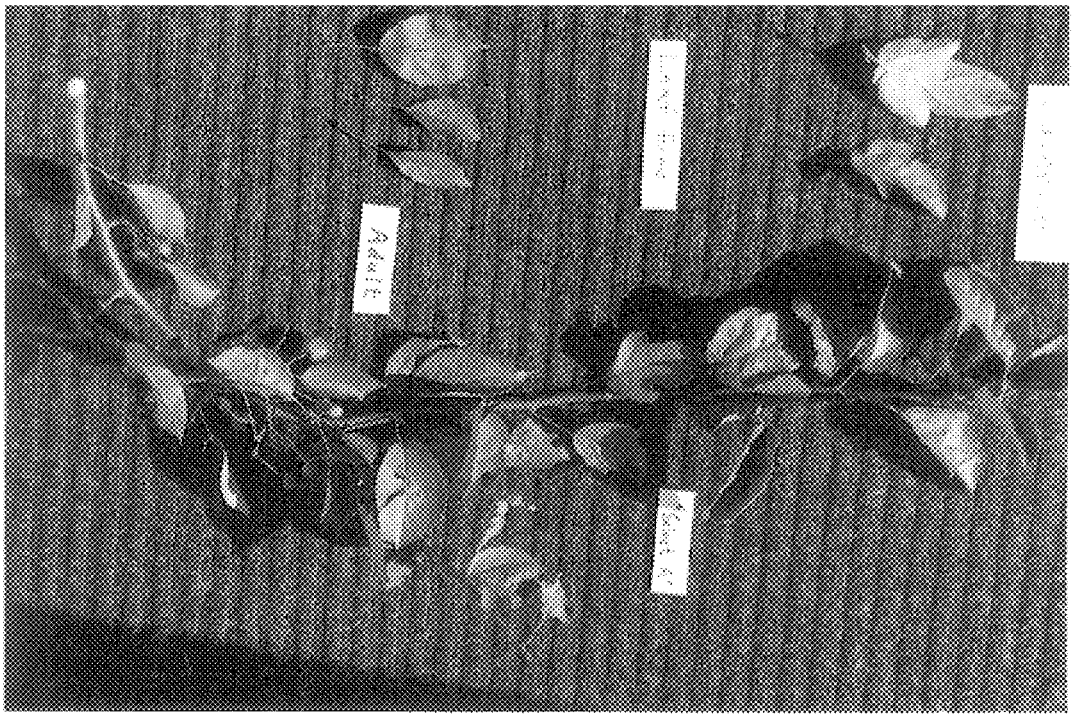

FIG. 5 demonstrates the two different leaf forms of the *Malus sargentii* 'Select A'. The juvenile leaf form most often appears on branches of vigorous current season's wood. (Most of the leaves in the top half of the photo are juvenile). The adult leaf form most often appears on branches of less vigor and branches older than 1 year. (Most of the leaves in the bottom half of the photo are adult).

Figure 6:
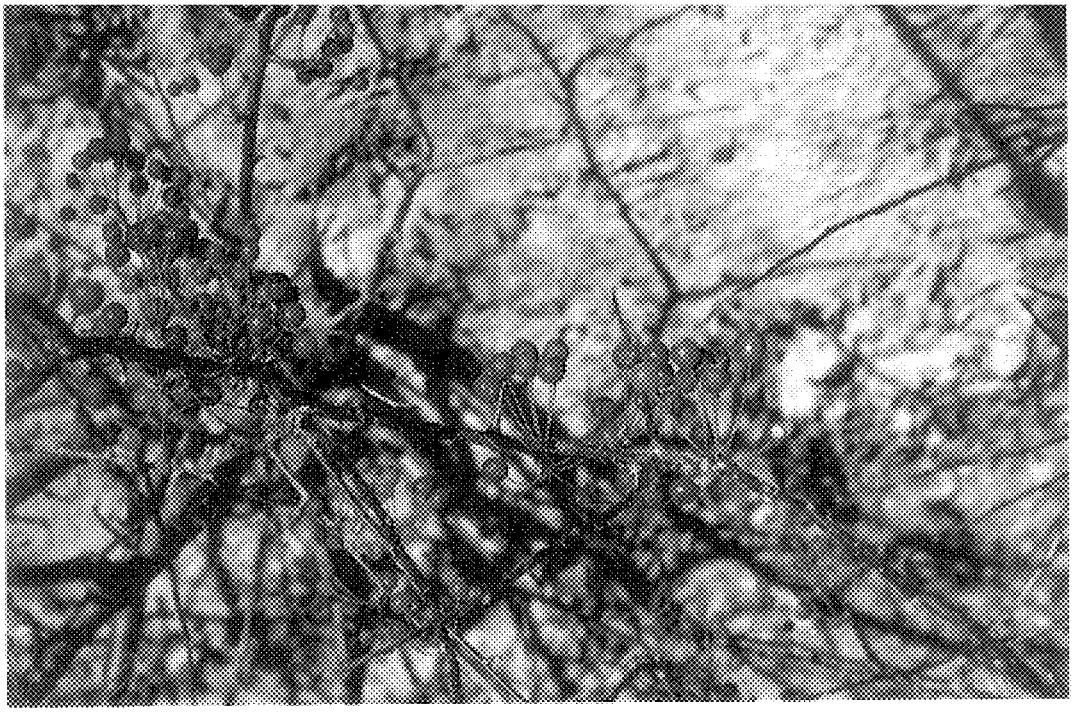

FIG. 6 shows fruit on *Malus sargentii* starting to shrivel. The photo was taken early December, 1998, the same day as the picture of FIG. 7.

Figure 7:
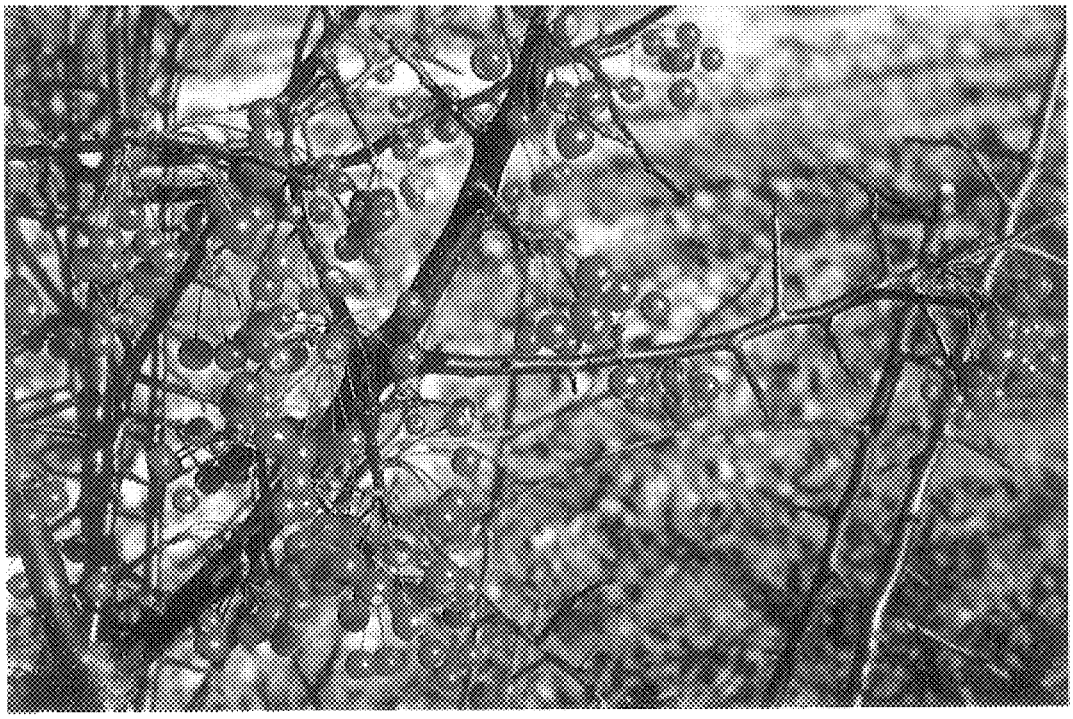

FIG. 7 shows fruit on *Malus sargentii* 'Select A' with no shriveling. The photo was taken early December, 1998, same day as the picture of FIG. 6.

Figure 8:
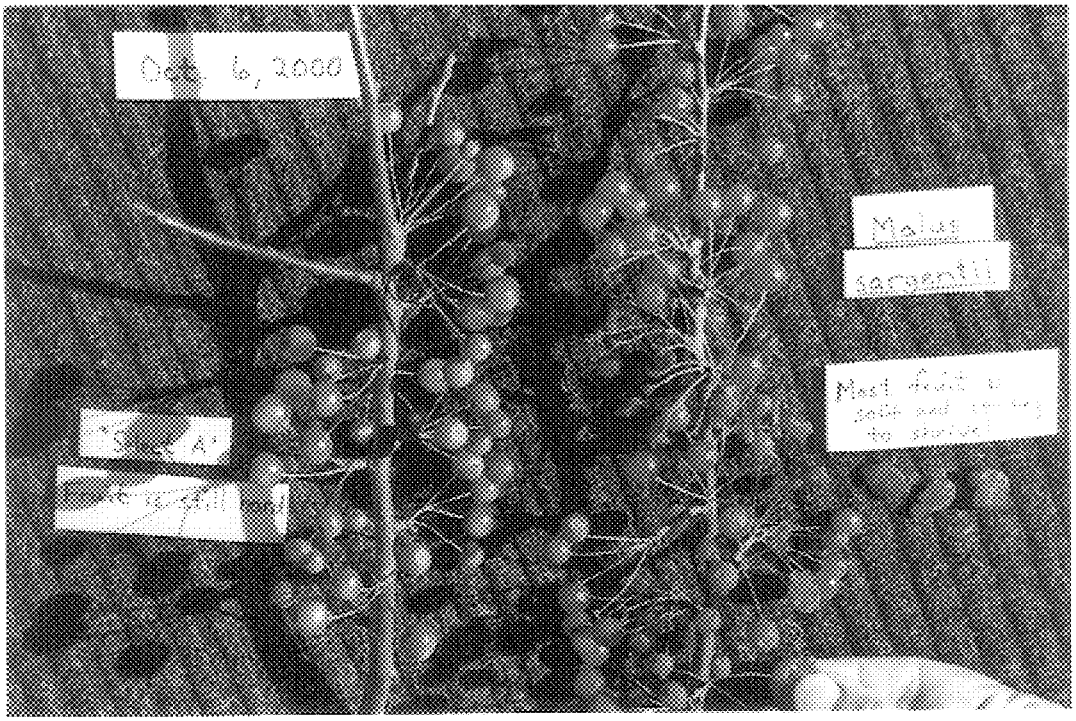

FIG. 8 shows fruiting branches of *Malus sargentii* and *Malus sargentii* 'Select A' side by side for comparison. Fruit of 'Select A' is still hard and cannot be squished. *Malus sargentii* is mostly soft, many are shriveling, and some have been taken by birds. The fruit is so soft it can easily be squished between one's fingers. Branches were picked and photographed on Oct. 6, 2000.

Figure 9:
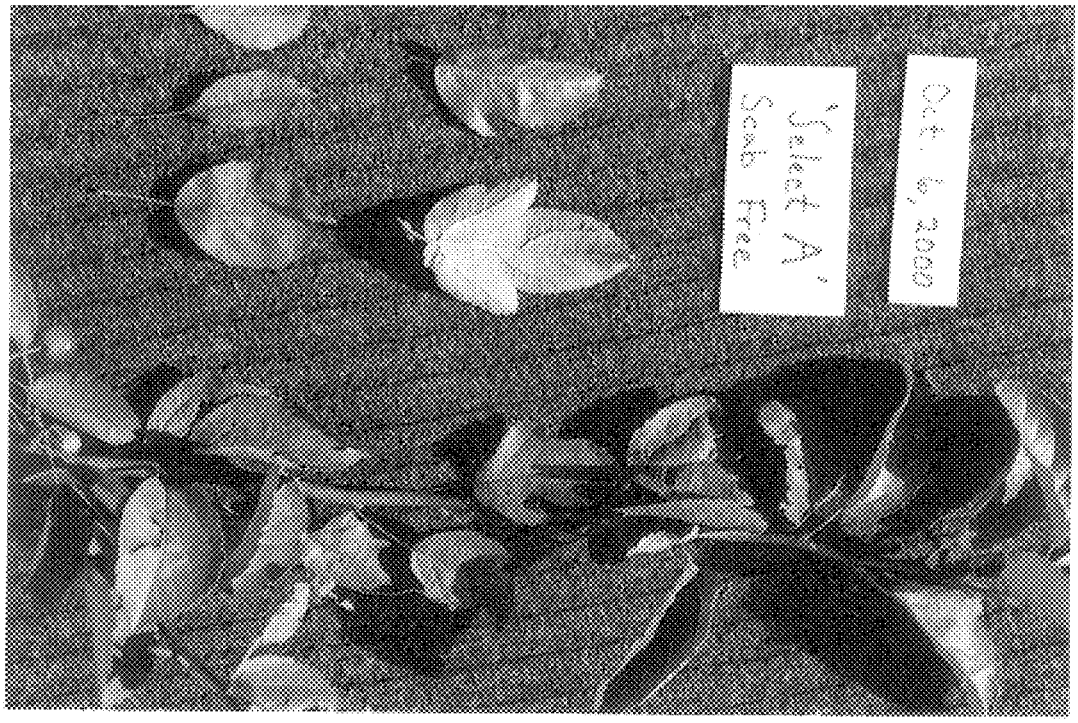

FIG. 9 shows juvenile (top left) and adult (bottom left) leaves of *Malus sargentii* 'Select A' that are scab free. No fungicides had been applied to the tree.

Figure 10:
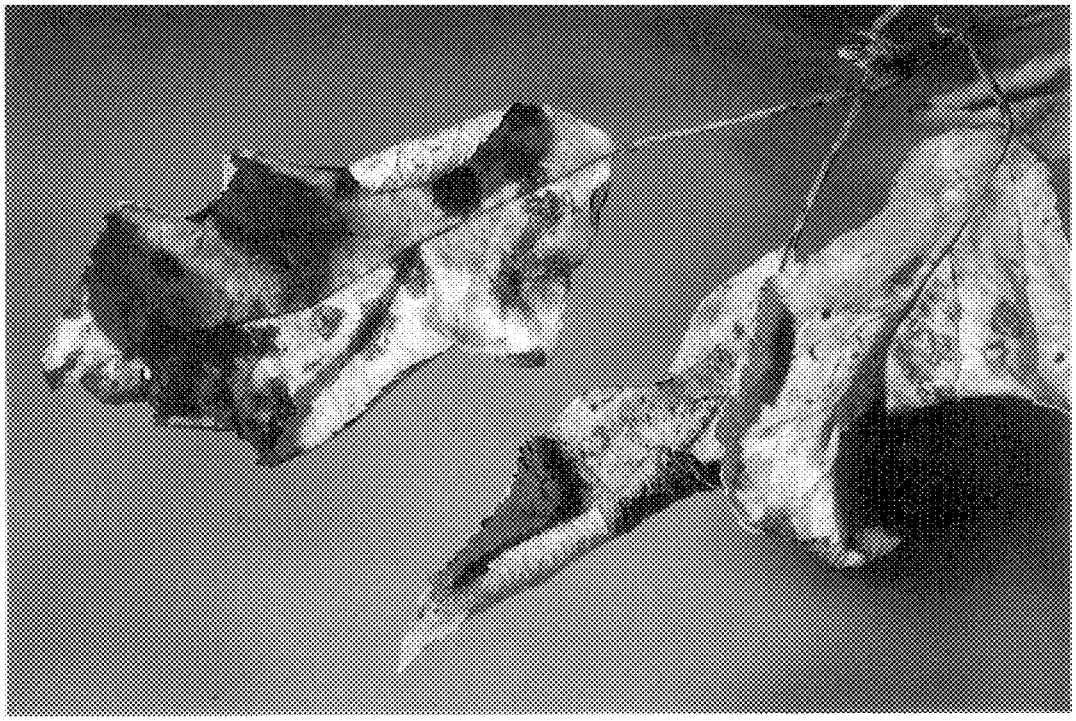

FIG. 10 shows leaves of an unknown crabapple with scab lesions.

Figure 11:
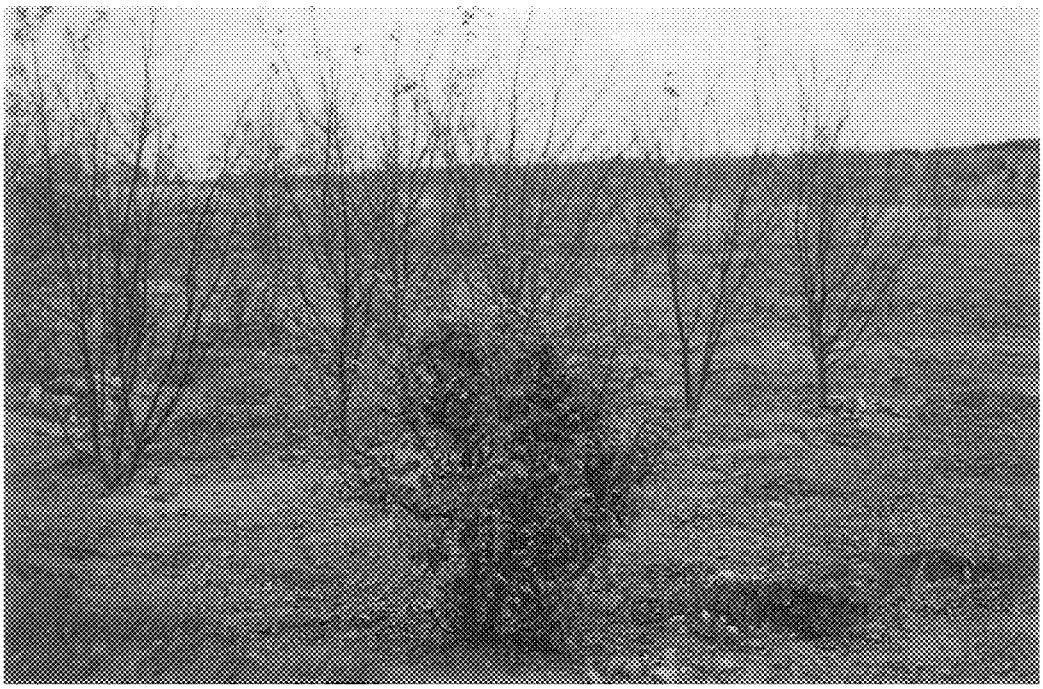

FIG. 11 shows a scab free *Malus sargentii* 'Select A' tree (own root) in the foreground. Background, Malus 'Profusion' defoliated due to scab. The photo was taken Oct. 6, 2000. No fungicides had been applied to the tree.

Figure 12:
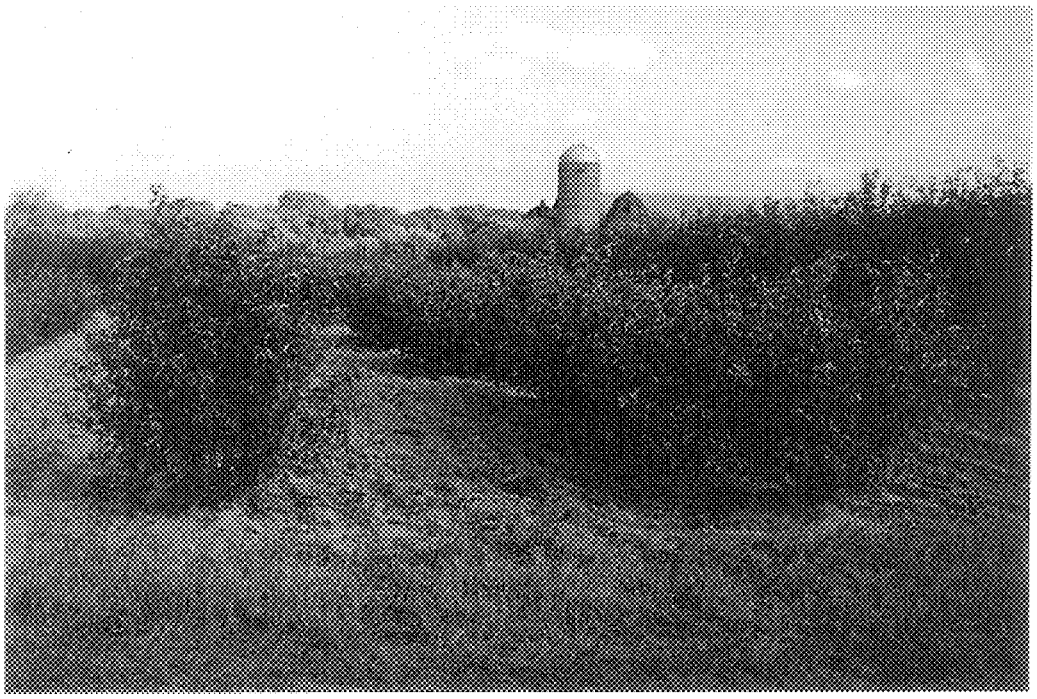

FIG. 12 compares the plants grown form rooted cuttings of both the parent (right) and 'Select A' (left) at six years maturity. The more upright, compact nature of the 'Select A' can be seen in comparison with the parent cutting grown plant. The photo was taken September, 1998.

Figure 13:
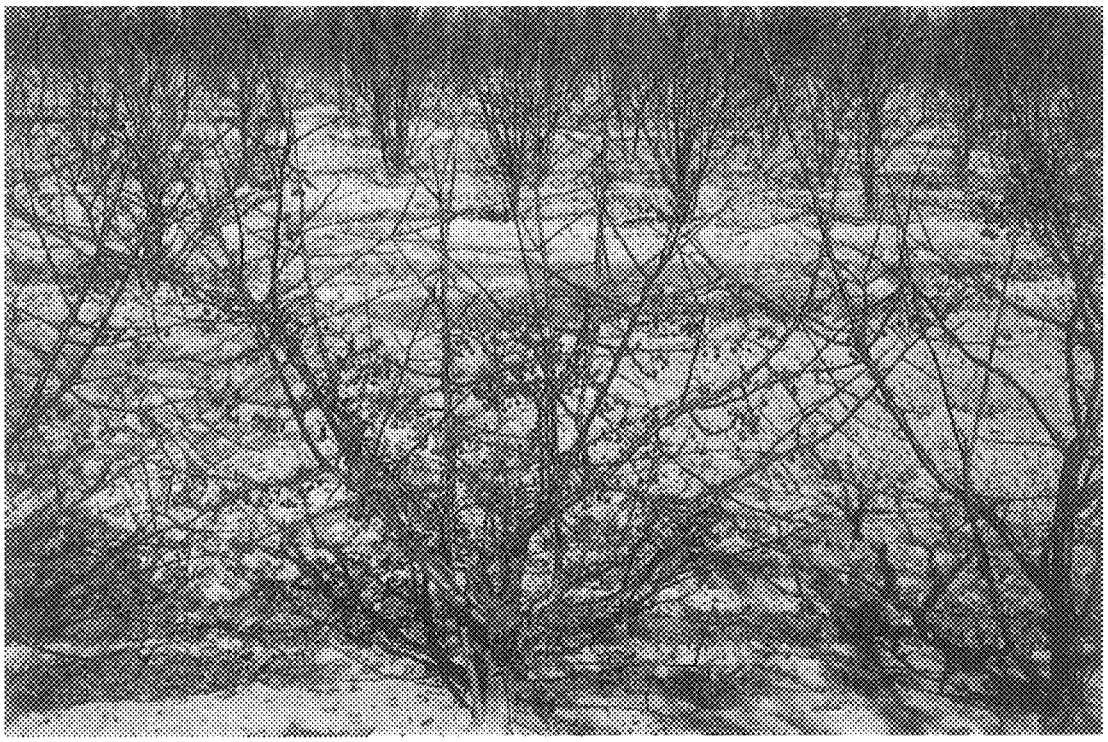

FIG. 13 shows a cutting grown plant of the parent *Malus sargentii* displaying its spreading, open, less compact habit at six years maturity. The photo was taken September, 1998.

Figure 14:
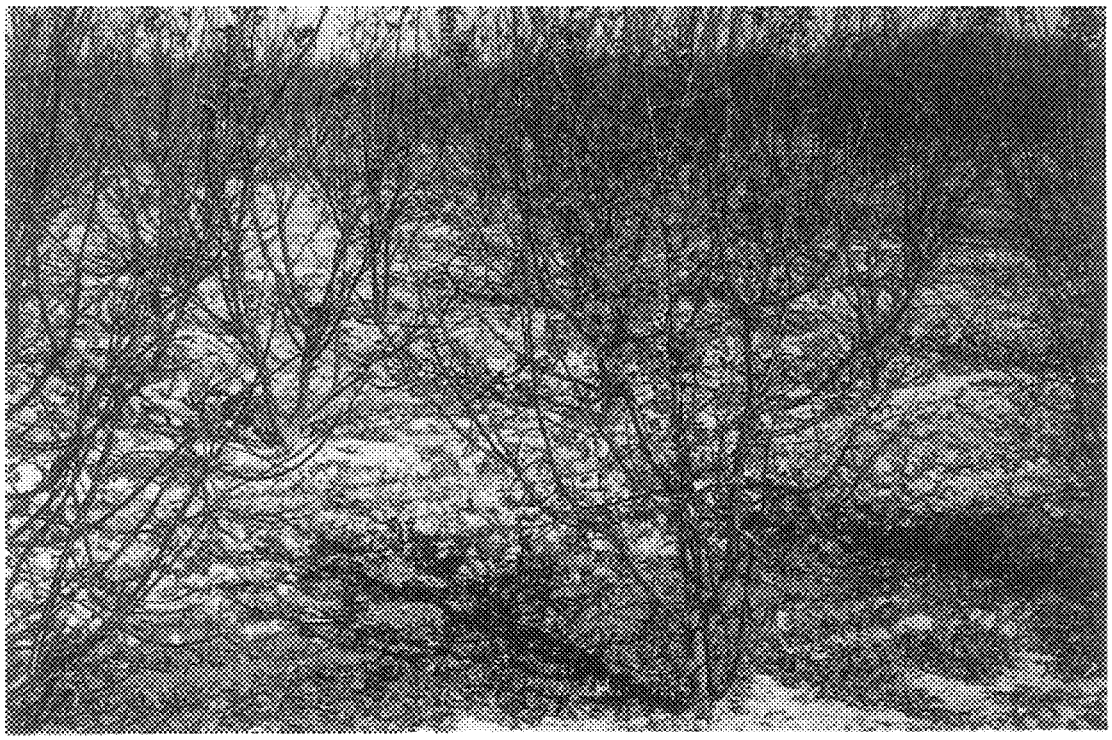

FIG. 14 shows a cutting grown plant of *Malus sargentii* 'Select A' displaying its compact, more upright habit at six years maturity. The photo was taken September, 1998.

Figure 15:
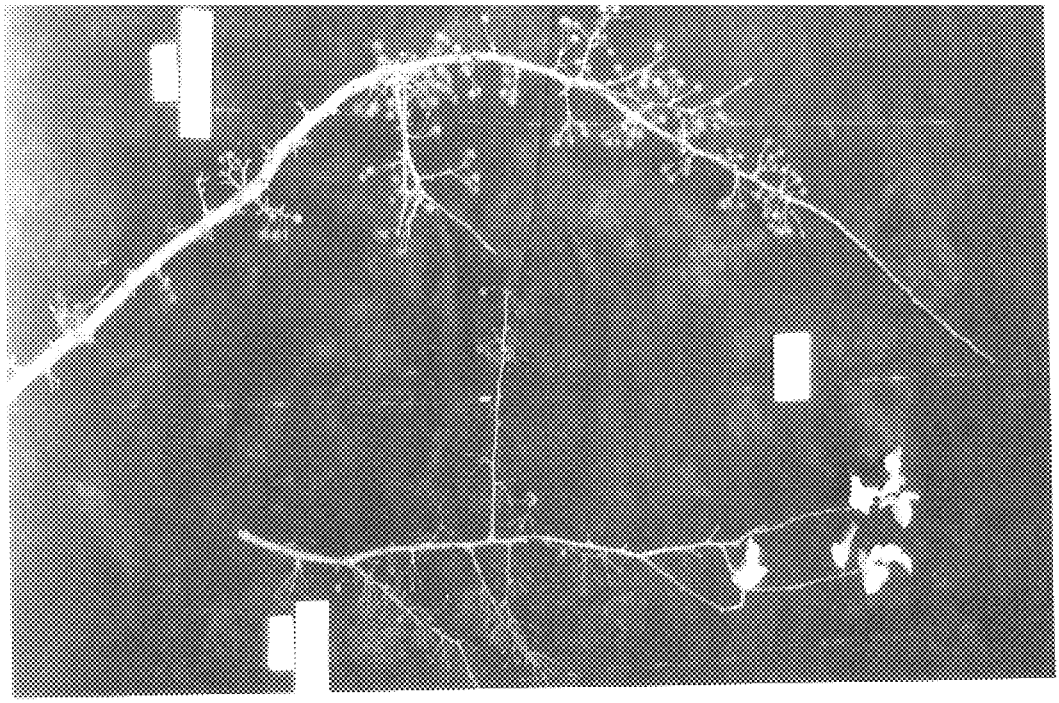

FIG. 15 shows branches cut from plants of eight years maturity of *Malus sargentii* 'Select A' and *Malus sargentii* (Parent Plant) produced from rooted cuttings. These are typical branches used for Example 1. The photo was taken Oct. 28, 2000. The fruit retention of both plants is typical of the varieties.

Figure 16:
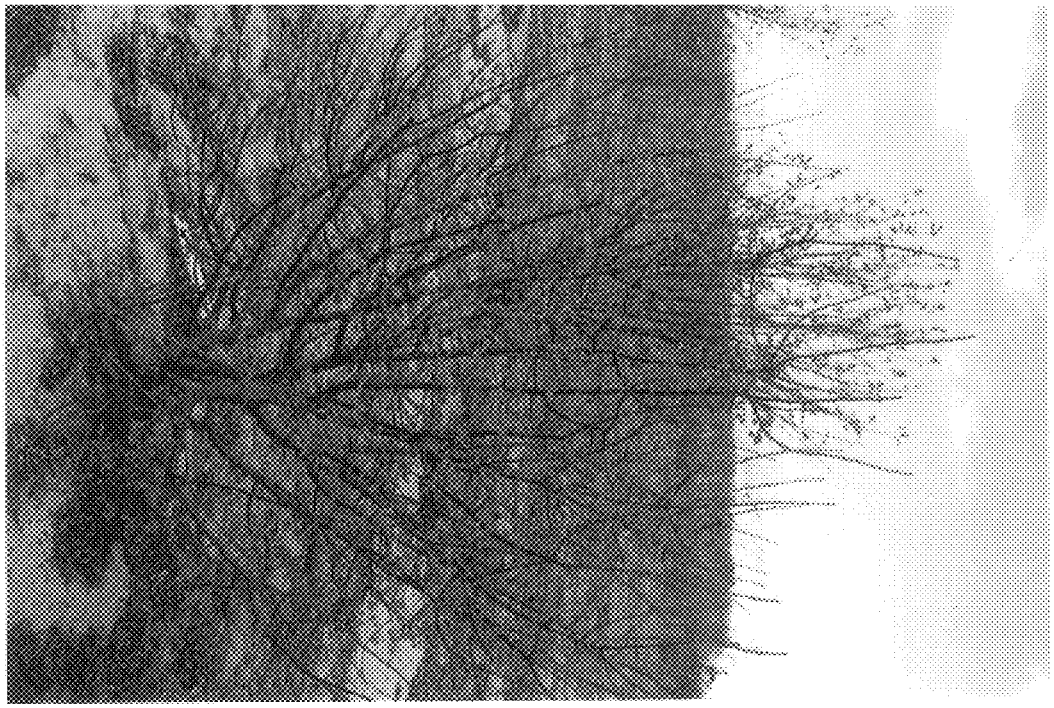
Figure 17:
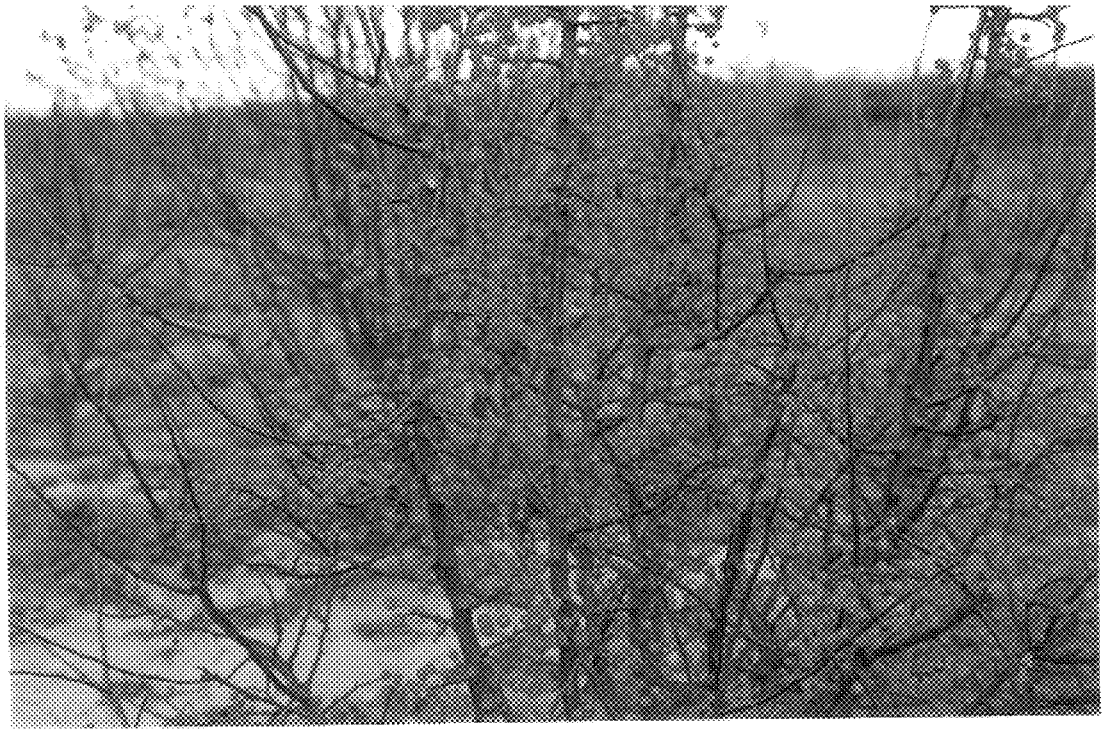

FIGS. 16 and 17 show plants of *Malus sargentii* 'Select A' of eight years maturity. The photographs were taken on Oct. 28, 2000. Fruit retention is typical of the variety. The upright nature of the young plant is easily recoginized in FIG. 14 when compared to FIG. 16. The trees were produced from rooted cuttings.

Figure 18:
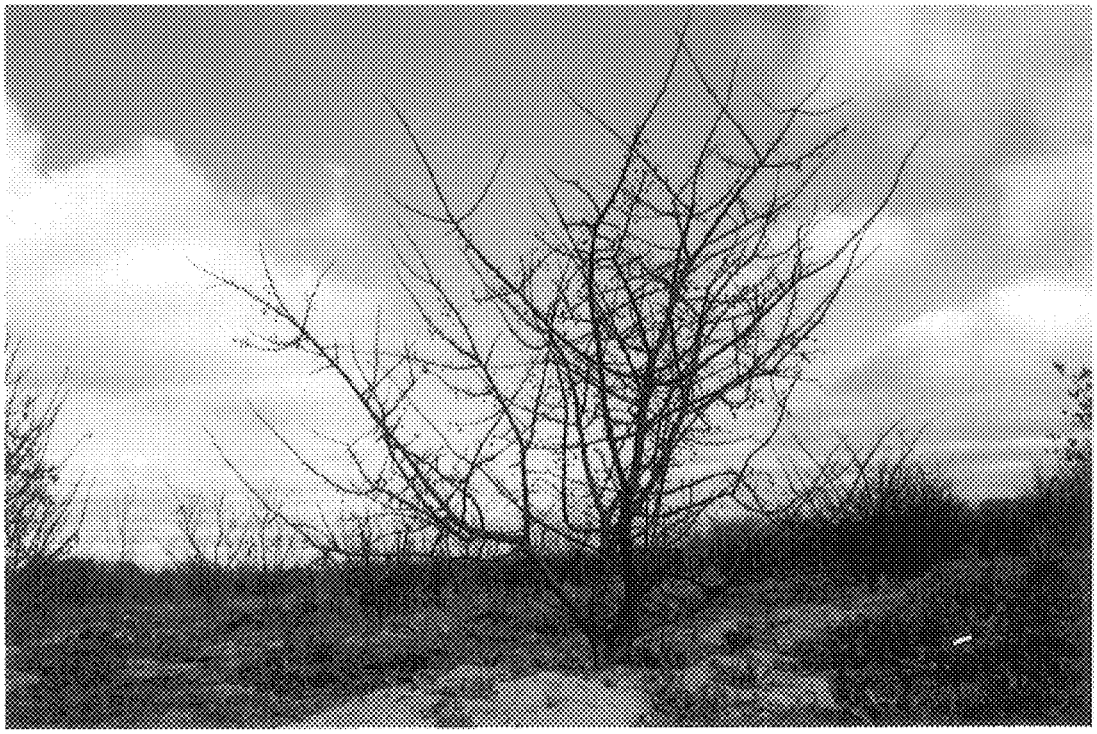
Figure 19:
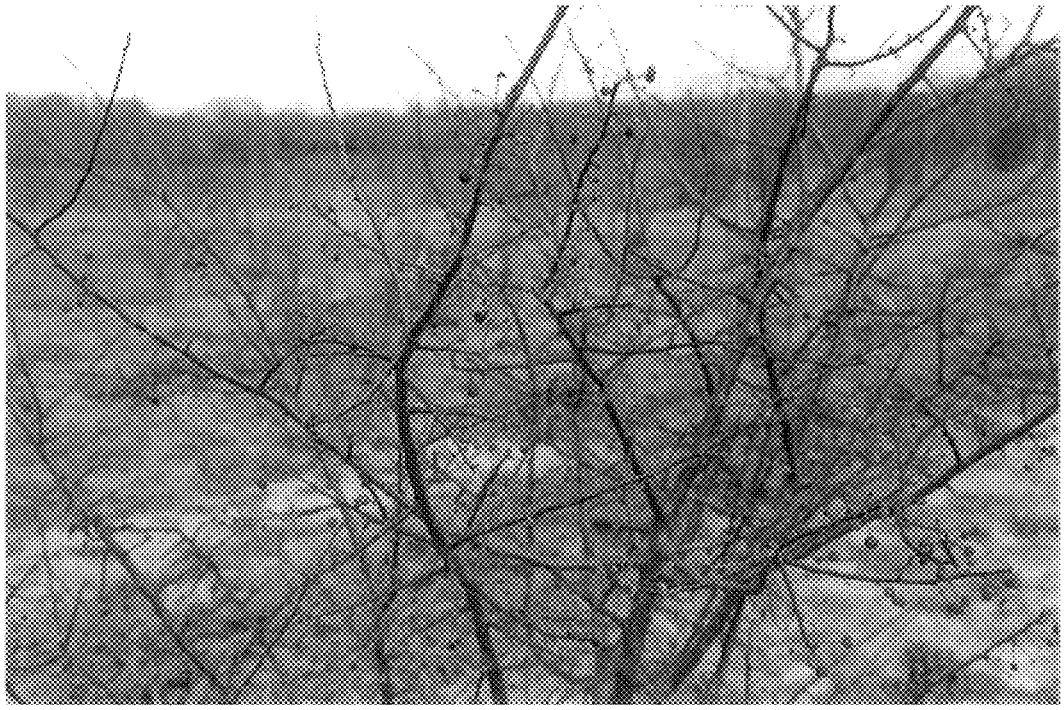

FIGS. 18 and 19 show *Malus sargentii* (Parent Plant) of eight years maturity. The photographs were taken on Oct. 28, 2000. The lack of fruit retention is typical of the variety. The spreading nature of the young *Malus sargentii* (Parent Plant) is easily recognized in FIG. 14 when compared with FIG. 16.

Figure 20:
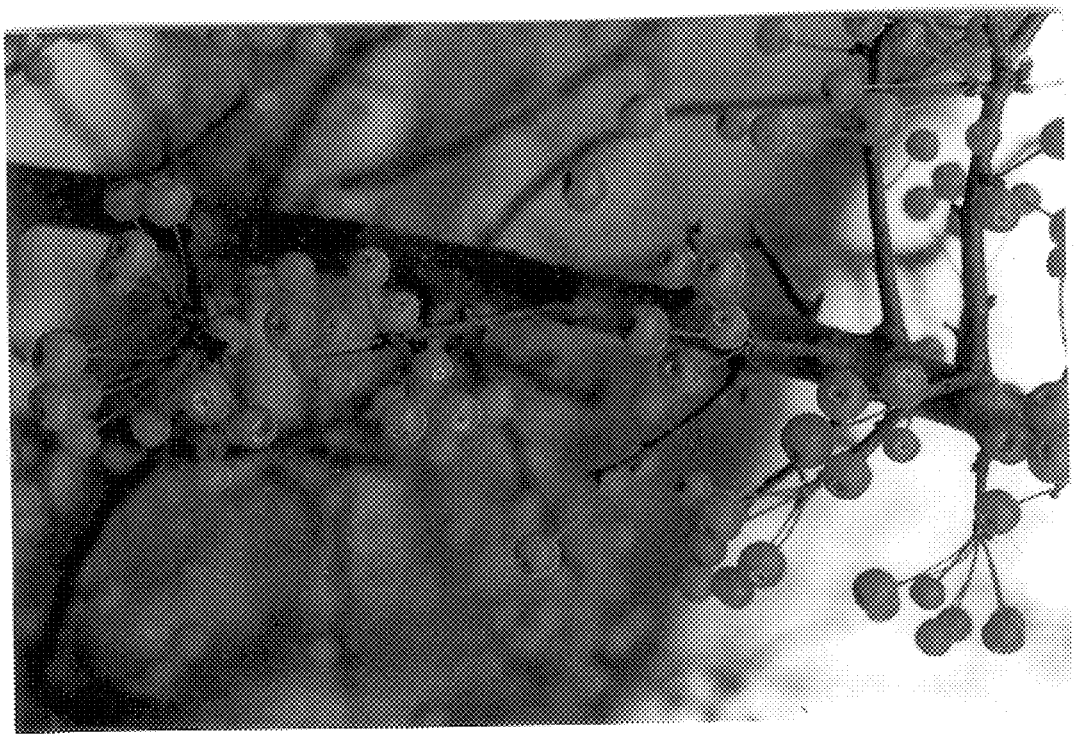

FIG. 20 shows fruit of *Malus sargentii* 'Select A' taken on Oct. 28, 2000. The Color and retention are typical of the variety.

Figure 21:
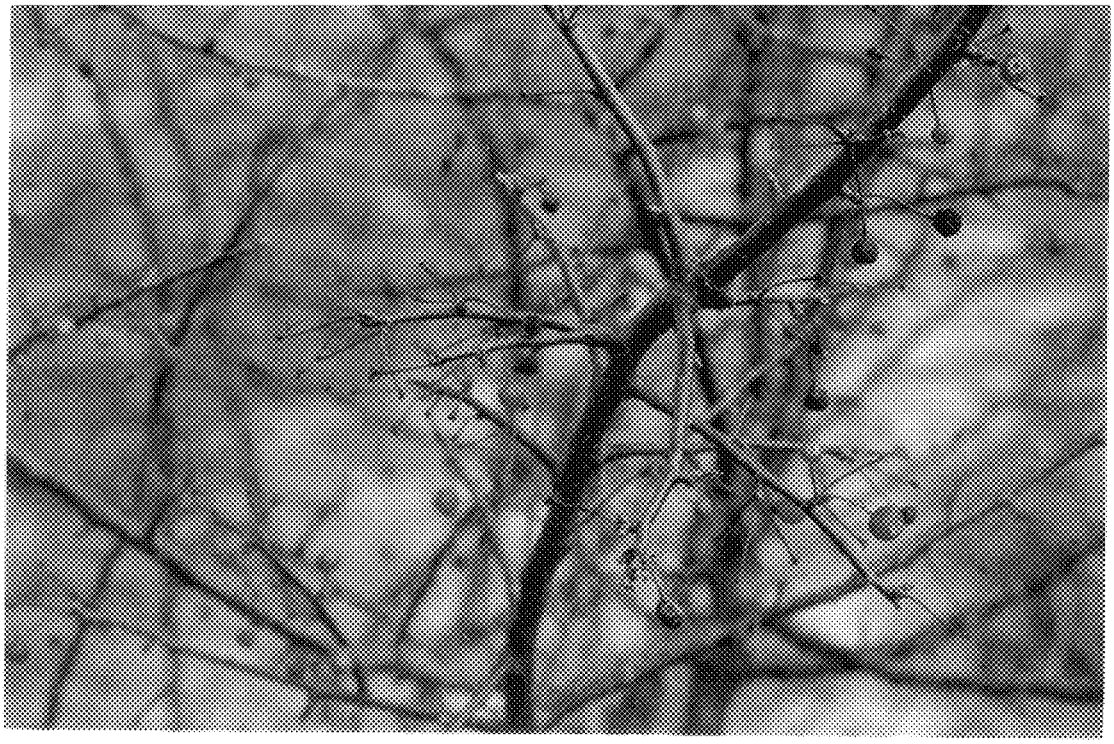

FIG. 21 shows fruit of *Malus sargentii* (Parent Plant) with eight years maturity. Much of the fruit has been stripped by birds.

DETAILED DESCRIPTION OF THE NEW VARIETY

The new tree is comparable in height and spread to its seed parent, *Malus sargentii*, in that it is a small tree which spreads wider than it grows tall and the new cultivar is resistant to Apple Scab disease. The new cultivar has demonstrated resistance to Apple Scab disease in Menominee Falls, Wis., Boring, Oreg. and St. Paul, Minn. The measure of resistance is based on the absence of scab lesions on the foliage.

It has similar leaf characteristics, especially the distinctive lobing on leaves arising from vigorous shoots, which is similar to its seed parent.

The fruit of the new variety has excellent color persistence when compared to the seed parent, indeed, the color persistence stays long into the winter season.

Further details of my new variety which I have chosen to identify for commercial purposes as "Select A" are set forth in the following description. The color terminology is in accordance with The Royal Horticulture Society Colour Chart (R.H.S.C.C.)

Parentage:
- *Seed parent.*—*Malus sargentii.*
- *Pollen parent.*—Unknown.

The new cultivar has demonstrated resistance to Apple Scab disease in Menomonee Falls, Wis., Boring, Oreg. and St. Paul, Minn. The measure of resistance is based on the absence of scab lesions on the foliage.

Tree:
- *Shape.*—Small, compact, spreader.
- *Height.*—5 feet tall, 8 feet wide.
- *Trunk size.*—4¼" diameter at 6 in. from ground for mature tree seventeen years old.
- *Trunk color.*—RHS 201A.
- *Bark.*—Mature is gray with ½ in. wide longitudinal plate, slightly exfoliating.
- *Bark color.*—2-year-old wood RHS 175A. 3-year-old wood RHS 199A. 4-year-old wood RHS 199B. 5-year-old wood RHS 199B.
- *Growth rate.*—5–8 in. of new stem growth per year.

Branches:
- *Angle of attachment.*—80 to 90 degrees.
- *Spacing.*—5 in. to about 12 in.
- *Size.*—1 in. to about 1¾ in. diameter.
- *Bark.*—2-year-old wood, reddish-brown Color, 3, 4, or 5 year old wood of gray-brown bark.
- *Lenticels.*—Size — 1/32 in.×1/64 in. latitudinal on one quarter inch branch 1/16 in×1/64 in. latitudinal on ¾ inch branch. Quantity—10–15 per 1 linear inch of branch.

Leaves

Two forms:
- *Juvenile foliage.*—From young, vigorous, juvenile branches; the leaves are three lobed with a prominent central lobe. The lobe tips are acute to cuspidate
- *Length.*—2½ to 2¾ in.
- *Width.*—1⅞ in. to 2¼ in.
- *Margins.*—Dentate.
- *Mature foliage.*—Adult foliage from mature adult branches; leaves are mostly elliptic or oval and cuspidate at the tip.
- *Length.*—2 in. to 3 in.
- *Width.*—1⅛ in. to 1½ in.
- *Margins.*—Dentate.
- *Both forms fall leaf color.*—RHS 13A — Smooth protruding mid-rib on underside.
- *Quality.*—Dense, heavy foliage, very clean, resistant to apple scab disease.
- *Color.*—Upper side R.H.S. group 146 A; Underside R.H.S. group 147C.
- *Pubescence*—Pubescence is present on the newest leaves of actively growing shoots. Present on both leaf forms. The foliage loses its pubescence as it ages. No pubescent is present in late September.

Flower buds:
- *Juvenile form.*—Diameter — 5/32 in. Length — ¼ in.
- *Mature form.*—Diameter — ¼ in. Length — ⅜ in.

*Form.*—Ovoid. Color — when sepals first divide RHS 58B. when sepals begin to unfurl at edge RHS 155D.

*Sepals.*—Curlback. Color — inside, RHS 138D. outside, RHS 144B.

*Calyx.*—Shape — 5 pointed star. Size — ⅜ in. Diameter, does not split.

*Aspect.*—Smooth on outside. Hairy on inside.

Flowers:

*Blooming period.*—Early to mid-May in southeast Wisconsin.

*Quality.*—Profuse.

*Size.*—Medium.

*Borne.*—Cluster.

*Shape.*—A cup when first opening changes later by slightly flattening.

*Petalage.*—Number of petals — 5. arrangement — polypetalous actinomorphic. margin — smooth.

*Color.*—Outside petal surface, base RHS 155D. Inside petal surface, base 155D. Reverse side of petal 155D.

*Texture.*—Soft.

*Appearance.*—Satiny.

*Peduncle.*—Length — 1¼ in. Color — R.H.S. yellow-green 151C.

*Fragrance.*—Slight, sweet.

*Flower descriptors.*—Inflorescence: Type — corymb. Dimensions: 2"–2¾" diameter across the top of the corymb. Quantity of flowers per corymb: 6–8 flowers. Sepals — not fused. Shape — isosceles triangle. Size — 5/32"×5/32"×3/32". Quantity — 5 sepals per flower. Petals dimensions: ½" wide by ⅝" long. Flower dimensions: 1⅛"–1¼" diameter across top of flower from petal tip to petal tip. Bloom time: Bud opening to petal fall lasts about ten days. Blooms late relative to other Malus taxa, with *Malus sargentii* 'Tina' and *Caragana arborescens* and after *Malus floribunda.*

Reproductive organs:

*Stamens, anthers.*—Arrangement — in center of flower surrounding Pistils. Length — Anthers — 1/16 in. total stamen — 9/32 in. Number — 20.

*Filaments.*—Length — ¼ in. Color — R.H.S. Green-White 157D.

*Pollen.*—Color — RHS 11A.

*Pistils.*—Length — 5/16 in. Number — 5.

*Ovaries.*—Color — RHS 154D. Length — 3/32 in. Diameter — 1/16 in.

Fruit:

*Size.*—Uniformly small.

*Axial diameter.*—11/32 in.

*Transverse diameter.*—7/16 in., no suture present.

*Form.*—Ventral surface — symmetrically rounded. Apen — 1/18 in. circular depression. Cavity — none.

*Stem.*—Size — ¾ in. to 1 in. Pubescence — none.

*Basin.*—Shape — slightly concave. Pubescence — none. Depth — 1/32 in. Breadth — 1/16 in.

*Calyx.*—Form — star like. Closure — completely triangular. Persistence — not persistent. Length — ⅛ in. Pubescence — none at maturity.

*Skin.*—Thickness — thin. Texture — smooth. Lenticels — none. Color — RHS 44A. Pubescence — none.

*Flesh.*—Texture — firm. Color — uniform RHS 22A.

Fruit descriptors:

*Time of fruit maturity.*—Fruit develops red color in mid to late September.

*Quantity of fruit produced.*—Approximately 38 fruits per linear foot of 2 and 3 year old wood.

This new variety of crabapple tree most nearly resembles its parent *Malus sargentii* in form, leaf characteristics and resistance to Apple Scab disease. It differs materially from its parent and other cultivated crabapple varieties particularly with respect to its compact, upright growth habit when young which spreads upon maturity as compared to its parent which has a more open spreading habit throughout its life. Its colorful, persistent fruit remains ornamental much later into the winter season than its parent.

The cultivar *Malus sargentii* 'Select A' differs from the known parent in two distinct ways:

(A) It has superior ornamental fruiting qualities later into the season. The majority of the small red fruit remain colorful on the tree in better condition than the parent.

FIG. 6 shows fruit on *Malus sargentii* starting to shrivel. The photo was taken early December, 1998.

FIG. 7 shows fruit on *Malus sargentii* 'Select A' with no shriveling. The photo was taken early December, 1998.

FIG. 8 shows fruiting branches of *Malus sargentii* and *Malus sargentii* 'Select A' side for comparison. Fruit of 'Select A' is still hard and cannot be squished. *Malus sargentii* is mostly soft, many are shriveling and some have been taken by birds. The photo was taken Oct. 6, 2000. Example (1) quantitatively explains the superior fruit persistence of *Malus sargentii* 'Select A'.

(B) The habit of the new cultivar is more compact than the parent.

FIG. 12 compares the plants grown form rooted cuttings of both the Parent (right) and 'Select A' (left) at six years maturity. The more upright, compact nature of the 'Select A' can be seen in comparison with the parent cutting grown plant. The photo was taken September, 1998.

FIG. 13 shows a cutting grown plant of the parent *Malus sargentii* displaying its spreading, open, less compact habit at six years maturity. The photo was taken September, 1998. Compare with FIG. 14.

The fruit of *Malus sargentii* (Parent plant) softens and is taken by birds early in the season when compared to *Malus sargentii* 'Select A'. Approximately 98.4% of the fruit remained on the tree of *Malus sargentii* 'Select A' on Oct. 28, 2000, while only about 9.7% remained on the *Malus sargentii* (Parent plant) tree. A comparison of the fruit of the trees is shown in Example 1.

The instant cultivar can be contrasted with the genus and species in which it is classified because it is an individual with several superior characteristics which are atypical of the species.

EXAMPLE 1

On Oct. 28, 2000, five branches were selected that were visually typical of all the branches on the trees of *Malus sargentii* 'Select A' (Original plant) and *Malus sargentii* (Parent plant). The branches included five year-old wood to current season's growth only.

The pedicel (fruit stalks) which had been stripped of fruit by birds and the pedicels with intact fruit on them were counted on the five select branches. Birds eat the fruit of crabapples once it softens. The following tables are the counts:

*Malus sargentii* (Parent Plant)

| | Quantity of Pedicels with and Without Intact Fruit | Quantity of Pedicels with Intact Fruit Only | % of Intact Fruit Remaining on Branches (10/28/00) |
|---|---|---|---|
| Branch 1 | 285 | 7 | 2.5 |
| Branch 2 | 273 | 24 | 8.8 |
| Branch 3 | 154 | 37 | 24.0 |
| Branch 4 | 163 | 17 | 10.4 |
| Branch 5 | 168 | 5 | 3.0 |
| Average % | — | — | 9.7 |

*Malus sargentii* 'Select A' (Original Plant)

| | Quantity of Pedicels with and Without Intact Fruit | Quantity of Pedicels with Intact Fruit Only | % of Intact Fruit Remaining on Branches (10/28/00) |
|---|---|---|---|
| Branch 1 | 182 | 180 | 98.9 |
| Branch 2 | 376 | 369 | 98.1 |
| Branch 3 | 281 | 278 | 98.9 |
| Branch 4 | 302 | 292 | 96.7 |
| Branch 5 | 176 | 175 | 99.4 |
| Average % | — | — | 98.4 |

I claim:

1. A new and distinct variety of hybrid crabapple tree substantially as herein shown and described, characterized by its compact, upright growth habit which spreads upon maturity and its Colorful persistent fruit that remains ornamental much later into the winter season than *Malus sargentii*.

* * * * *